(12) United States Patent
Lachapelle et al.

(10) Patent No.: US 9,491,300 B2
(45) Date of Patent: *Nov. 8, 2016

(54) HANDLING CONCURRENT SPEECH

(71) Applicant: GOOGLE INC., Mountain View, CA (US)

(72) Inventors: Serge Lachapelle, Vallentuna (SE); Alexander Kjeldaas, Saltsjö-Boo (SE)

(73) Assignee: GOOGLE INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/059,222

(22) Filed: Mar. 2, 2016

(65) Prior Publication Data

US 2016/0182728 A1 Jun. 23, 2016

Related U.S. Application Data

(63) Continuation of application No. 14/027,061, filed on Sep. 13, 2013, now Pat. No. 9,313,335.

(60) Provisional application No. 61/701,520, filed on Sep. 14, 2012.

(51) Int. Cl.
*H04M 3/56* (2006.01)
*A61B 18/24* (2006.01)
(Continued)

(52) U.S. Cl.
CPC .......... *H04M 3/568* (2013.01); *A61B 17/3203* (2013.01); *A61B 17/3207* (2013.01);
(Continued)

(58) Field of Classification Search
CPC ....... G10L 19/20; G10L 25/90; G10L 19/00; G10L 15/20; H04L 2012/6481
USPC .................. 370/260, 428; 704/275, E15.001
See application file for complete search history.

(56) References Cited

U.S. PATENT DOCUMENTS 8,085,803 B2 * 12/2011 Hoban .................... H04L 43/16
370/428
2005/0114129 A1 * 5/2005 Watson ................... G10L 15/26
704/235
(Continued)

FOREIGN PATENT DOCUMENTS

DE    102006002603.9    7/2007
JP    2006-229903    8/2006

OTHER PUBLICATIONS

Ang, Automatic Dialog Act Segmentation and Classification in Multiparty Meetings, 2005 IEEE ICASSP, Philadelphia, PA, Mar. 18-23, 2005, pp. 1061-1064.
(Continued)

*Primary Examiner* — Charles C Jiang
*Assistant Examiner* — Will Lin
(74) *Attorney, Agent, or Firm* — Morgan, Lewis & Bockius LLP

(57) ABSTRACT

A system having one or more processors and a memory receives both speech data from first and second participants of a session. The system outputs the speech of the first participant. The system outputs the speech of the second participant concurrent with the speech of the first participant when the length of time of the speech data of the first participant is more than a predetermined threshold amount. The system outputs the speech data of the second participant in accordance with an adjustment of the speech of one or more participants of the session that includes delaying output of the speech data of the second participant until after the speech data of the first participant has been outputted when the length of time of the speech data of the first participant is less than the predetermined threshold amount.

20 Claims, 10 Drawing Sheets

(51) Int. Cl.
    *A61B 17/3211*     (2006.01)
    *A61B 17/3207*     (2006.01)
    *A61B 17/3203*     (2006.01)
    *G10L 21/00*     (2013.01)
    *A61B 17/50*     (2006.01)
    *A61N 1/05*     (2006.01)
    *H04L 29/06*     (2006.01)
    *G10L 17/00*     (2013.01)
    *A61B 17/32*     (2006.01)

(52) U.S. Cl.
    CPC ... *A61B17/3211* (2013.01); *A61B 17/320725* (2013.01); *A61B 17/50* (2013.01); *A61B 18/245* (2013.01); *A61B 90/02* (2016.02); *A61N 1/056* (2013.01); *G10L 21/00* (2013.01); *H04L 65/403* (2013.01); *A61B 2017/320044* (2013.01)

(56) References Cited

U.S. PATENT DOCUMENTS

| | | |
|---|---|---|
| 2007/0053352 A1 | 3/2007 | Corcoran |
| 2009/0150151 A1* | 6/2009 | Sakuraba ............ G10L 21/028 704/246 |
| 2011/0202345 A1* | 8/2011 | Meyer ................. G10L 13/033 704/260 |
| 2011/0271210 A1 | 11/2011 | Jones et al. |

OTHER PUBLICATIONS

Google, International Search Report and Written Opinion, PCT/US2013/059786, Mar. 13, 2014, 13 pgs.

Google, International Preliminary Report on Patentability, PCT/US2013/059786, Mar. 17, 2015, 10 pgs.

* cited by examiner

HANDLING CONCURRENT SPEECH

CROSS REFERENCE TO RELATED APPLICATIONS

The present application claims priority to U.S. patent application Ser. No. 14/027,061, filed Sep. 13, 2013, which claims priority to U.S. Provisional Patent Application No. 61/701,520, filed Sep. 14, 2012, each of which is hereby incorporated by reference herein in its entirety.

TECHNICAL FIELD

The disclosed embodiments relate generally to systems and methods for handling concurrent speech in a session in which some speech is delayed in order to alleviate speech overlap in the session.

BACKGROUND

The disclosed embodiments relate generally to distributed client-server computer network systems, and in particular, to a system and method for handling concurrent speech. Every day, hundreds of conferences, teleconferences in particular, are held. Unlike those at an in-person conference, attendees at a teleconference often join and speak from different geographical locations. Due to a lack of visual cues and other reasons, however, attendees at a teleconference are more likely to speak at or around the same time, resulting in simultaneous, concurrent or otherwise overlapping speaking. Despite the increased likelihood of this overlapping speaking, users of a teleconferencing system still expect their communication with other users to be orderly and effective.

In conferencing systems, when many attendees speak at or around a same time, a speaker's speech may not be heard for an extended period, until after all "early" speech has been outputted. The extended delays often result in user frustration and confusion, as the speaker tries to speak again or to ascertain whether the conferencing system has suffered an error or data loss. The situation is exacerbated when a speech is frequently interrupted, and must be repeated numerous times before it is fully delivered, reducing the effectiveness of the conferencing systems.

SUMMARY

The problems with conventional approaches to handle concurrent speaking described above are reduced or eliminated by the disclosed systems and methods described below.

In many situations it is advantageous to provide systems and methods that selectively eliminate concurrent speech, but still meets users' perception that their speech is appropriately processed or delivered. In particular, an approach that selectively adjusts the output of a particular participant's speech, based on an attribute of speech of one or more other participants, can increase the effectiveness of a conferencing system, without the attendant costs of broadcasting a large number of participants' speech in a serial first-in first-out manner.

In some embodiments, a method is performed at a server system having one or more processors and memory storing one or more programs for execution by the one or more processors so as to perform the method. The method includes receiving speech data from a first participant of a session, receiving speech data from a second participant of the session, and outputting the speech of the first participant. The method further includes outputting the speech of the second participant in accordance with an adjustment of the speech of a participant of the session when the speech of the second participant temporally overlaps less than a first predetermined threshold amount of a terminal portion of the speech of the first participant, and dropping the speech of the second participant when the speech of the second participant temporally overlaps more than the first predetermined threshold amount of the terminal portion of the speech of the first participant. In some embodiments, the method optionally includes outputting the speech of the second participant in accordance with an adjustment of the speech of a participant of the session by delaying output of the speech of the second participant.

In accordance with some embodiments, a computer system (e.g., a client system or server system) includes one or more processors, memory, and one or more programs. The one or more programs are stored in memory and configured to be executed by the one or more processors and the one or more programs include instructions for performing the operations of the method described above. In accordance with some embodiments, a non-transitory computer readable storage medium has stored therein instructions which when executed by one or more processors, cause a computer system (e.g., a client system or server system) to perform the operations of the methods described above.

BRIEF DESCRIPTION OF THE DRAWINGS

For a better understanding of the disclosed embodiments, reference should be made to the Description of Embodiments below, in conjunction with the following drawings in which like reference numerals refer to corresponding parts throughout the figures.

DESCRIPTION OF EMBODIMENTS

It will be understood that, although the terms "first," "second," etc. may be used herein to describe various elements, these elements should not be limited by these terms. These terms are only used to distinguish one element from another. For example, a first participant could be termed a second participant, and, similarly, a second participant could be termed a first participant, without changing the meaning of the description, so long as all occurrences of the "first participant" are renamed consistently and all occurrences of the "second participant" are renamed consistently. The first participant and the second participant are both participants, but they are not the same participant.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The embodiments described below include client and server systems, which typically inter-operate in a distributed client-server system and corresponding methods of handling concurrent speech, where some portion of the concurrent speech is dropped, or adjusted so as to handle concurrent speech efficiently and effectively.

Figure 1:
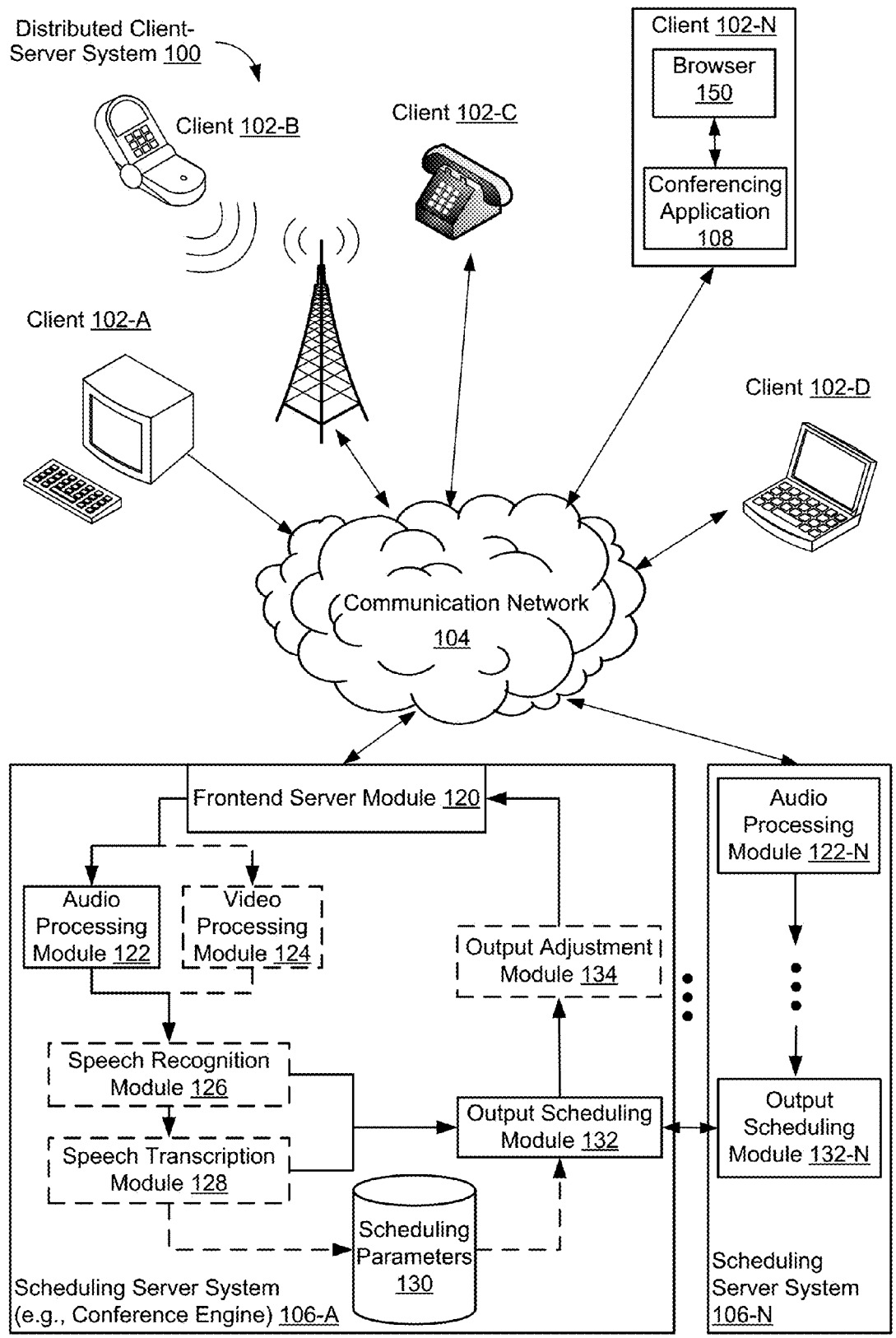
FIG. 1 is a block diagram illustrating a distributed client-server system, in accordance with some embodiments.

FIG. 1 includes a block diagram illustrating a Distributed Client-Server System 100 for handling concurrent speech. Distributed Client-Server System 100 includes one or more Client System(s) 102 (a representative of which is referred to herein as "Client 102"), one or more Scheduling Server System(s) 106-A . . . 106-N (a representative of which is referred to herein as "Scheduling Server 106"), and Communication Network 104 for connecting Client(s) 102 to Scheduling Server(s) 106. Communication Network 104 optionally includes the Internet, one or more local area networks (LANs), one or more wide area networks (WANs), other types of networks, or a combination of such networks.

Client 102 optionally includes Browser 150 and/or Conferencing Application 108. In some embodiments, Conferencing Application 108 is part of Browser 150. In some embodiments, Browser 150 is a general purpose Internet browser (sometimes called a Web browser) having a browser window used for communication—audio communication and/or video communication, e.g., speech—with other users of a conferencing system. A web application user interface is optionally implemented using hypertext markup language (HTML) or extensible markup language (XML) elements that are rendered by Browser 106. Alternatively, a user communicates with other users of the conferencing system via standalone Conferencing Application 108. After a user begins her communication (audio and/or video) with other users, via Browser 150 or stand-alone Conferencing Application 108, Client 102 relays speech data—which, in some embodiments, includes audio and/or video information (or a portion thereof), and corresponding meta-data (for example, timestamp, length of a communication, formatting data)—to Scheduling Server 106 via Communication Network 104. In some embodiments, Scheduling Server 106 processes the speech data and, optionally, transmits the speech data to one or more other Scheduling Servers 106 for parallel or serial processing. Once the speech data (including the audio/video information, and corresponding meta-data) is processed by one or more Scheduling Servers 106, it is transmitted back to one or more Client(s) 102, where the audio and/or video communication (e.g., one or more speech) is delivered to their respective users. In some embodiments, Client 102 is a telephone. In some embodiments, Scheduling Server 106 is implemented, in software (e.g., programming package) or hardware (e.g., IC chip), on Client 102. In some embodiments, for example, where Scheduling Server 106 is implemented on Client 102, speech data is transmitted among Clients 102, without going through a centralized server. In some embodiments, speech is outputted differently at one Client 102, than at another Client 102, for example, with different amounts of delay, or at different speeds.

In some embodiments, a consensus algorithm is used among Clients 102 to collect information from Clients 102, such as, which speech or portion thereof was delivered or ignored at which Client(s) 102, and for how long speech is delayed at one or more particular Clients 102. In some embodiments, the consensus algorithm also provides to Scheduling Server 106, in accordance with the information collected, one or more scheduling options (e.g., client feedback) that can offer best overall performance among several Clients 102. In some embodiments, the information collected by the consensus algorithm (including scheduling options) are stored in Scheduling Parameters 130, after they are transmitted to Scheduling Server 103, for future speech scheduling. In some embodiments, to avoid or minimize disparity between the manner in which speech is delivered at several Clients 102, which could result in user confusion, Scheduling Server 106 dynamically adjusts speech output, in accordance with the information provided by the consensus algorithm. In some embodiments, Scheduling Server 102 dynamically adjusts speech output, so that Clients 102 (continuously) converge to a state where, either speech is delivered at least at more than a predefined number of Clients 102, or speech being delivered at several Clients 102 is substantially the same (in terms of output speed, and ordering of speech).

In some embodiments, Scheduling Server 106 includes Frontend Server Module 120, Audio Processing Module 122, Video Processing Module 124, Speech Recognition Module 126, Speech Transcription Module 128, Scheduling Parameters 130, Output Scheduling Module 132, and Output Adjustment Module 134. In some embodiments, Frontend Server Module 120 receives speech data from one or more Clients 102, and relays them to Audio Processing Module 122, Video Processing Module 124, or both. In some embodiments, Frontend Server Module 120 also transmits output speech received from Output Scheduling Module 132 or Output Adjustment Module 134 to one or more Client(s) 102 for delivery. In some embodiments, Frontend Server Module 120 also modifies the speech data by converting audio/video information therein into a format that can be readily processed by Scheduling Server 106. Audio Processing Module 122 extracts audio information, and, optionally, corresponding meta-data from speech data, and transmits them to Output Scheduling Module 132 or Speech Recognition Module 126. In some embodiments, Video Processing Module 124 extracts video information and corresponding meta-data, from speech data, and, optionally, transmits them to Output Scheduling Module 132 or Speech Recognition Module 126. In some embodiments, Audio Processing Module 122 and Video Processing Module 124 output audio and/or video information, and optional corresponding meta-data to Speech Recognition Module 126. In some embodiments, Speech Recognition Module 126 uses speech recognition techniques (implemented in hardware or software) to recognize letters, words, phrases, terms, sentences, changes of speech tone or facial expression etc., in the audio and/or video information, in accordance with speech meta-data. In some embodiments, Speech Transcription Module 128 transcribes the audio information and/or audio portion of the video information, into text, in accordance with speech meta-data. Scheduling Parameters 130 includes output scheduling information, such as speech classifications, speech priorities, and speaker roles. Output Scheduling Module 132 receives audio and/or video information and outputs speech at a predetermined time, in accordance with speech meta-data, and/or Scheduling Parameters 130. Optionally, Output Scheduling Module 132 determines the predetermined output time based at least in part on information received from Speech Recognition 126, Speech Transcription 128, and Scheduling Parameters 130. Output Adjustment Module 134, optionally, adjusts output speech, e.g., adding further delays, removing existing delays, enlarging or shortening pauses within a speech, and increasing or decreasing speech speed using one or more pitch conserving algorithms. In some embodiments, delaying speech is achieved by recording the speech, and playing back the recorded speech after a predetermined time interval, optionally at a faster or slower speed than the original speech.

In some embodiments, where there are multiple server systems (e.g., Scheduling Server 106-A . . . Scheduling Server 106-N), speech data from Client 102, or a portion thereof, is transmitted to two or more Scheduling Servers 106 for parallel or serial processing and scheduled output. In some embodiments, Output Scheduling Modules 132 (e.g., Output Scheduling Module 132-A . . . Output Scheduling Module 132-N), within the multiple server systems, communicate with each other to coordinate speech output. In some embodiments, speech data received from Client 102 is partitioned into several portions, of equal or different length, and different portions of a same speech are transmitted to different server systems and in particular different Audio Processing Module(s) 122 (e.g., Audio Processing Module 122-A . . . Audio Processing Module 122-N), where they are processed and scheduled for output.

Figure 2:
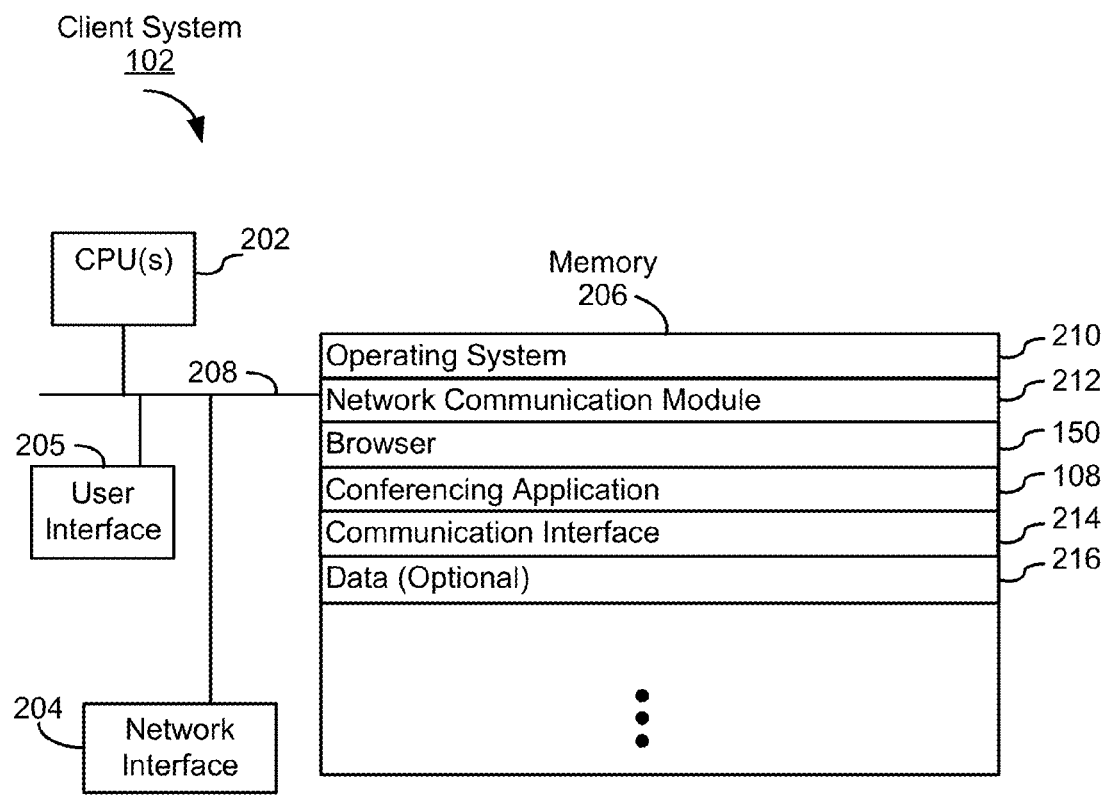
FIG. 2 is a block diagram illustrating a client system, in accordance with some embodiments.

FIG. 2 is a block diagram illustrating Client System 102 (also referred to herein as "Client 102") in accordance with some embodiments. Client 102 typically includes one or more processing units CPU(s) 202 (also herein referred to as processors), one or more network or other Communication Interfaces 204, Memory 206, User Interface 205 comprising a display device and a keyboard, mouse, touchpad, touch screen or other input device, and one or more Communication Buses 208 for interconnecting these components. Communication Buses 208 optionally include circuitry (sometimes called a chipset) that interconnects and controls communications between system components. Memory 206 typically includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 206 optionally includes one or more storage devices remotely located from CPU(s) 202. Memory 206, or alternatively the non-volatile memory device(s) within Memory 206, comprises a non-transitory computer readable storage medium. In some embodiments, Memory 206 or alternatively the non-transitory computer readable storage medium stores the following programs, modules and data structures, or a subset thereof:

- Operating System 210 that includes procedures for handling various basic system services and for performing hardware dependent tasks;
- Network Communication Module (or instructions) 212 for connecting Client 102 to other computers (e.g., Scheduling Servers 106 or other Clients 102) via one or more Network Interfaces 204 (wired or wireless) and one or more Communication Networks 104 (FIG. 1), such as the Internet, other wide area networks, local area networks, metropolitan area networks, and so on;
- Browser 150 for loading web pages, which optionally includes code for executing or interpreting Conferencing Application 108 as an embedded application web page(s);
- Conferencing Application 108—e.g., a stand-alone conferencing client or an embedded program in Web Browser 150 (e.g., a internet browser plug-in)—for transmitting user communications (audio and/or video, e.g., speech) from Client 102 to one or more Scheduling Servers 106, and receiving communications from one or more Scheduling Servers 106 for delivery at Client 102;
- Communication Interface 214 for transmitting speech data, including audio and/or video information, and corresponding meta-data, to one or more Scheduling Servers(s) 106, and receiving output speech (audio and/or video, and corresponding meta-data) from Scheduling Servers(s) 106, via Communication Network 104; and
- optionally, Data 216 includes cached speech data (e.g., recently received or recorded audio/video information, corresponding meta-data, scheduling information, etc.) associated with one or more user communications.

In some implementations, one or more of the above identified elements are stored in one or more of the previously mentioned memory devices, and corresponds to a set of instructions for performing a function described above. The above identified modules or programs (e.g., sets of instructions) need not be implemented as separate software programs, procedures or modules, and thus various subsets of these modules may be combined or otherwise re-arranged in various embodiments. In some embodiments, Memory 206 optionally stores a subset of the modules and data structures identified above. Furthermore, Memory 206 may store additional modules and data structures not described above.

Figure 3:
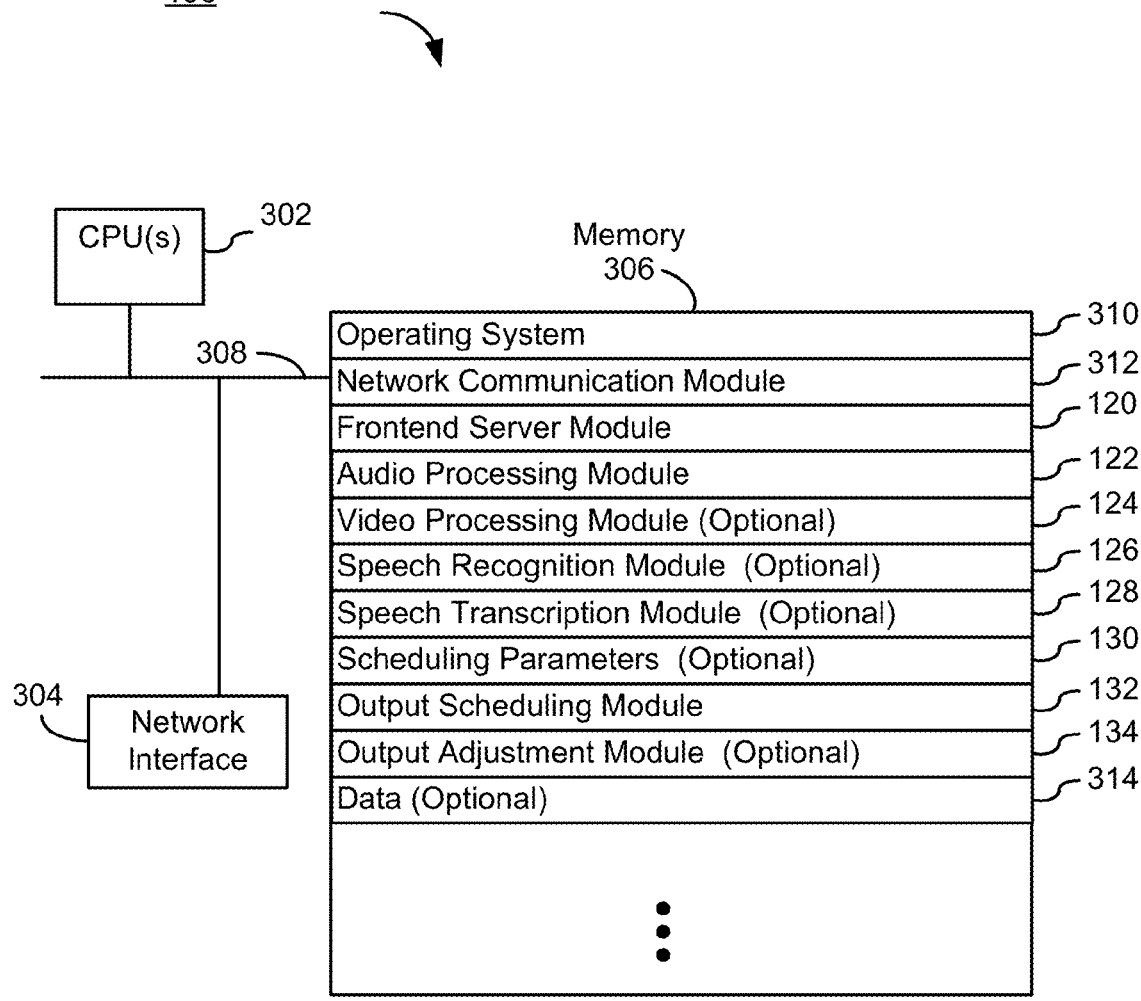
FIG. 3 is a block diagram illustrating a server system, in accordance with some embodiments.

FIG. 3 is a block diagram illustrating Conferencing Scheduling Server System 106 (also herein referred to as "Scheduling Server 106"), in accordance with some embodiments. Scheduling Server 106 typically includes one or more processing units CPU(s) 302 (also herein referred to as processors), one or more network or other Communications Interfaces 308, Memory 306, and one or more Communication Buses 308 for interconnecting these components. Communication Buses 308 optionally include circuitry (sometimes called a chipset) that interconnects and controls communications between system components. Memory 306 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 306 optionally includes one or more storage devices remotely located from CPU(s) 302. Memory 306, or alternatively the non-volatile memory device(s) within Memory 306, comprises a non-transitory computer readable storage medium. In some embodiments, Memory 306 or alternatively the non-transitory computer readable storage medium stores the following programs, modules and data structures, or a subset thereof:

- Operating System 310 that includes procedures for handling various basic system services and for performing hardware dependent tasks;
- Network Communication Module (or instructions) 312 for connecting Scheduling Server 106 with other computers (e.g., Clients 102, or other Scheduling Servers 106) via one or more Network Interfaces 304 (wired or wireless) and one or more Communication Networks 104 (FIG. 1), such as the Internet, other wide area networks, local area networks, metropolitan area networks, and so on;
- Frontend Server Module 120 for receiving and relaying speech data to Audio Processing Module 122 and/or Video Processing Module 124, in parallel or in a predefined sequence, and transmitting output speech to one or more Client(s) 102 for delivery;
- Audio Processing Module 122 for processing audio information included in speech data, in accordance with corresponding meta-data, and transmitting audio information and/or corresponding meta-data to Speech Recognition Module 126 for further processing, or alternatively to Output Scheduling Module 132 for output;
- optionally, Video Processing Module 124 for processing video information included in speech data, in accordance with corresponding meta-data, and transmitting video information and/or corresponding meta-data to Speech Recognition Module 126 for further processing, or alternatively to Output Scheduling Module 132 for output;
- optionally, Speech Recognition Module 126 for recognizing letters, words, phrases, terms, or sentences, changes of speech tones or facial expressions of an attendee etc. in the audio and/or video information, in accordance with the corresponding meta-data;
- optionally, Speech Transcription Module 128 for transcribing audio information and/or video information, into corresponding text, in accordance with the corresponding meta-data;
- optionally, Scheduling Parameters 130 that includes, past or current scheduling information concerning speech classifications, speech/speaker priorities, speaker roles, historical participant behaviors (e.g., whether a participant has generally been a slow or fast speaker, and whether a participant has a past tendency to speak in long sessions without interruption), and client feedback;
- Output Scheduling Module 132 for outputting speech (audio and/or video information) at a predetermined time, in accordance with corresponding meta-data, and/or information received from Speech Recognition Module 126, Speech Transcription Module 128, and Scheduling Parameters 130;
- optionally, Output Adjustment Module 134 for adjusting output speech, for example, by adding further delays, removing existing delays, enlarging or shortening pauses within a speech, and increasing or decreasing speech speed using a pitch conserving algorithm, as described in greater detail below with reference to FIGS. 7-10; and
- optionally, Data 314 which includes cached speech data (e.g., recently received speech data, speech awaiting scheduling output, etc.) associated with one or more user communications.

In some implementations, one or more of the above identified elements are stored in one or more of the previously mentioned memory devices, and corresponds to a set of instructions for performing a function described above. The above identified modules or programs (e.g., sets of instructions) need not be implemented as separate software programs, procedures or modules, and thus various subsets of these modules may be combined or otherwise re-arranged in various embodiments. In some embodiments, Memory 306 optionally stores a subset of the modules and data structures identified above. Furthermore, Memory 306 optionally stores additional modules and data structures not described above.

Although FIG. 3 shows a "Scheduling Server System 106," FIG. 3 is intended more as functional description of the various features which may be present in a set of servers than as a structural schematic of the embodiments described herein. In practice, and as recognized by those of ordinary skill in the art, items shown separately could be combined and some items could be separated. For example, some items shown separately in FIG. 3 could be implemented on single servers and single items could be implemented by one or more servers. The actual number of servers used to implement a "Scheduling Server System 106" and how features are allocated among them will vary from one implementation to another, and optionally depends in part on the amount of data traffic that the system must handle during peak usage periods as well as during average usage periods.

Figure 4:
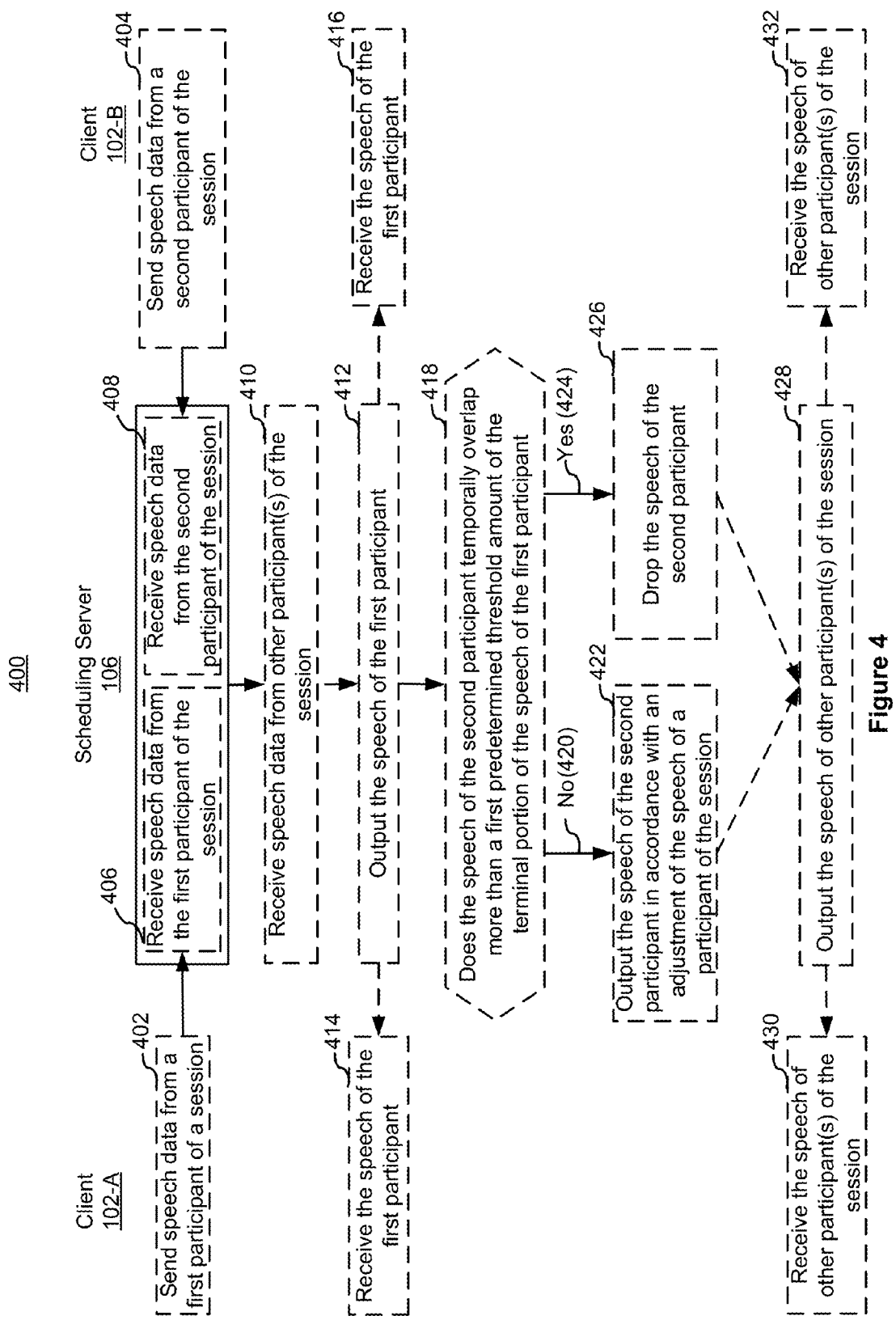
FIG. 4 includes a flow chart illustrating a client-server system for handling concurrent speech, in accordance with some embodiments.

FIG. 4 includes a flowchart illustrating a method for handling, at a server system, concurrent speech received from client systems, and outputting speech, or a portion thereof, with adjustments, in accordance with some embodiments. Method 400 is, optionally, governed by instructions that are stored in a non-transitory computer readable storage medium and that are executed by one or more processors of one or more servers (e.g., Scheduling Server 106 in FIG. 3). Operations shown in FIG. 4 typically correspond to instructions stored in a computer memory or non-transitory computer readable storage medium (e.g., Memory 306 of Scheduling Server 106 in FIG. 3). In some implementations, the non-transitory computer readable storage medium includes a magnetic or optical disk storage device, solid state storage devices such as Flash memory, or other non-volatile memory device or devices. In some implementations, the computer readable instructions stored on the non-transitory computer readable storage medium include one or more of: source code, assembly language code, object code, or other instruction format that is interpreted or executed by one or more processors. In various embodiments, some operations in method 400 may be combined and/or the order of some operations may be changed from the order shown in FIG. 4.

In some embodiments, Client 102-A sends (402), to Scheduling Server 106, speech data from a first participant of a session (e.g., a teleconferencing session established between Client(s) 102 and Scheduling Server (106). In some embodiments, within a predefined threshold time interval (e.g., at or around the same time), Client 102-B also sends (404), to Scheduling Server 106, speech data from a second participant of the session. Scheduling Server 106 then receives speech data from both the first participant of the session (406), and the second participant of the session (408). In some embodiments, concurrent speech includes both speech made, at Clients 102, within a threshold time interval, and speech received, by Scheduling Server 106, within the threshold time interval. In some embodiments, after receiving speech data from the first and second participants, Scheduling Server 106 also receives (410) speech data from other participant(s) of the session (e.g., a third and/or fourth participant of the session). Scheduling Server 106 then outputs (412) the speech of the first participant to one or more Clients 102. In some embodiments, after the speech of the first participant is outputted, both Client 102-A (414) and Client 102-B (416) receive the speech of the first participant. In some implementations, the speech of the first participant is received by Clients 102 in a predefined sequence. In some embodiments, the predefined sequence is determined based at least in part on Scheduling Parameters 130, and meta-data (e.g., speaker priority, speaker identify, length of a speech, etc.) included in the speech data. Alternatively, in other implementations, the speech of the first participant is received by Clients 102-A and 102-B at substantially the same time.

In some embodiments, after outputting the speech from the first participant, Scheduling Server 106 determines (418) whether the speech of the second participant temporally overlaps more than a first predetermined threshold amount of the terminal portion of the speech of the first participant. In some embodiments, if the speech of the second participant does not (420 "No") temporally overlap more than the first predetermined threshold amount of the terminal portion of the speech of the first participant, Scheduling Server 106 outputs the speech of the second participant in accordance with an adjustment of the speech of a participant of the session. In other words, if the speech of the first and second participants does not overlap each other, or the overlap is less than the first predetermined threshold, the speech of the second participant is outputted with adjustments. In some embodiments, the predetermined threshold amount is a threshold period time having a duration selected from the range of 100 milliseconds to 1000 milliseconds. In some embodiments, the first predetermined threshold amount is a threshold period time having a duration selected from the range of 1 second to 10 seconds. In some embodiments, the predetermined threshold amount is a threshold period time having a duration selected from the range of 5 seconds to 40 seconds. In some embodiments, the predetermined threshold amount is 10, 20, 30, 40, 50, 60, 70, or 80 milliseconds, or greater than 1 second.

In some embodiments, speech is temporally adjusted by Scheduling Server 106, without a user involvement. In other embodiments, speech is temporally adjusted by both users and Scheduling Server 106. In some embodiments, user temporal adjustments and temporal adjustments by Scheduling Server 106 are assigned different priorities. When a user temporal adjustment conflicts with an adjustment by Scheduling Server 106, a high priority temporal adjustment overrides a low priority adjustment.

In some embodiments, speech of a single participant is adjusted. In other embodiments, speech of two or more participants of the session is adjusted. In some embodiments, the speech of the second participant is temporally adjusted; in other embodiments, speech of participant(s) other than the first and second participants is adjusted. In some embodiments, the speech of the first participant is temporally adjusted. The temporal adjustment of speech is described in greater detail below with references to FIGS. 7-10.

In some embodiments, if the speech of the second participant does (424 "Yes") temporally overlaps more than the first predetermined threshold amount of the terminal portion of the speech of the first participant, Scheduling Server 106 drops (426) the speech of the second participant. In other words, if the speech of the first and the second participants overlaps more than the first predetermined threshold, the speech of the second participant is dropped. In some embodiments, dropping speech includes not outputting the speech to one or more participants of the session. In other embodiments, dropping speech includes outputting the speech to some but not all participants of the session—for example, outputting the speech to participants other than the first or the second participant, or outputting the speech to the original speaker, but not to other participants of the session. This approach increases the effectiveness of a conferencing system, because concurrent or overlapping speech is reduced or eliminated by selectively dropping speech that overlaps other speech. This approach also meets the user perception that their speech is properly processed, when the dropped speech is outputted to its original speaker so that speakers always hear (or views) their own speech. In some embodiments, the predetermined threshold amount is a threshold period time having a duration selected from the range of 100 milliseconds to 1000 milliseconds. In some embodiments, the first predetermined threshold is a threshold period time having a duration selected from the range of 1 second to 10 seconds. In some embodiments, the first predetermined threshold is a threshold period time having a duration selected from the range of 5 seconds to 40 seconds. In some embodiments, the first predetermined threshold is 10, 20, 30, 40, 50, 60, 70, or 80 milliseconds, or greater than 1 second.

In some embodiments, after the speech of the second participant is outputted or dropped, Scheduling Server 106 outputs (428) the speech of other participant(s) of the session (e.g., speech of the third participant) to one or more Clients 102. After it is outputted, in some embodiments, the speech of other participant(s) (e.g., the third participant) is received by Client 102-A (430), and Client 102-B (432), and delivered to their respective users.

In some embodiments, when the speech of the third participant temporally overlaps, at least partially, with both the speech of the first participant and that of the second participant, the outputting of speech of the second participant in accordance with an adjustment of the speech of a participant of the session comprises: outputting the speech of the second participant before the speech of the third participant when a priority of the second participant in the session is higher than a priority of the third participant. In other words, if the speech of the third participant overlaps the speech of both the first participant and the second participant, Scheduling Server 106 outputs the speech of the second participant in accordance with an adjustment of the speech of a participant of the session, such as outputting the speech of the second participant before the speech of the third participant, when the second participant is associated with a higher priority (e.g., the second participant is considered a higher priority speaker), than the third participant. In some other embodiments, the priorities of the second and the third participants are determined on a First-In-First-Out (FIFO) basis, a role-based basis (e.g., main speaker, interrupting speaker, etc.), a social network status basis, or a number of votes. An example of a social network status basis is the relationship between the interrupting speakers (e.g., the second speaker, the third speaker) and the first speaker. In one example of the use of a social network status basis to determine speaker priority, the speech of the interrupting speaker that is deemed to have a closer relationship to the first speaker will be played first and the speech of the other interrupting speakers will be played later or dropped. In another example, the speech of the interrupting speaker that is deemed to have closer relationships overall to the participants of the session will be played first and the speech of the other interrupting speakers will be played later or dropped. In still another example of the use of a social network status basis to determine speaker priority, the speech of the interrupting speaker that has received the most votes (e.g., the most "likes") during the session by other participants in the session to have a closer relationship to the first speaker will be played first and the speech of the other interrupting speakers will be played later or dropped. In such an example, the priority of a speaker in the session can actually increase if others like what the speaker is saying during the session and affirmatively vote or approve the speaker. In one such instance, participants can cast more than one vote for another speaker. In another instance, participants can cast more than one vote for another speaker of the session in each predetermined time interval in the session (e.g., one vote per minute allowed per participant).

It should be understood that the particular order in which the operations in FIG. 4 have been described are merely exemplary and are not intended to indicate that the described order is the only order in which the operations could be performed. One of ordinary skill in the art would recognize various ways to reorder the operations described herein. Additionally, it should be noted that details of other processes described herein with respect to method 500 (described herein with reference to FIG. 5) are also applicable in an analogous manner to method 400 described above with respect to FIG. 4. For example, the speech data and its receipt thereof, speech and its output thereof, adjusting or dropping of a speech, and speech overlapping described above with reference to method 400 may have one or more of the characteristics of the speech data and its receipt thereof, speech and its output thereof, adjusting or dropping of a speech, and speech overlapping described herein with reference to method 500. For brevity, these details are not repeated here.

Figure 5:
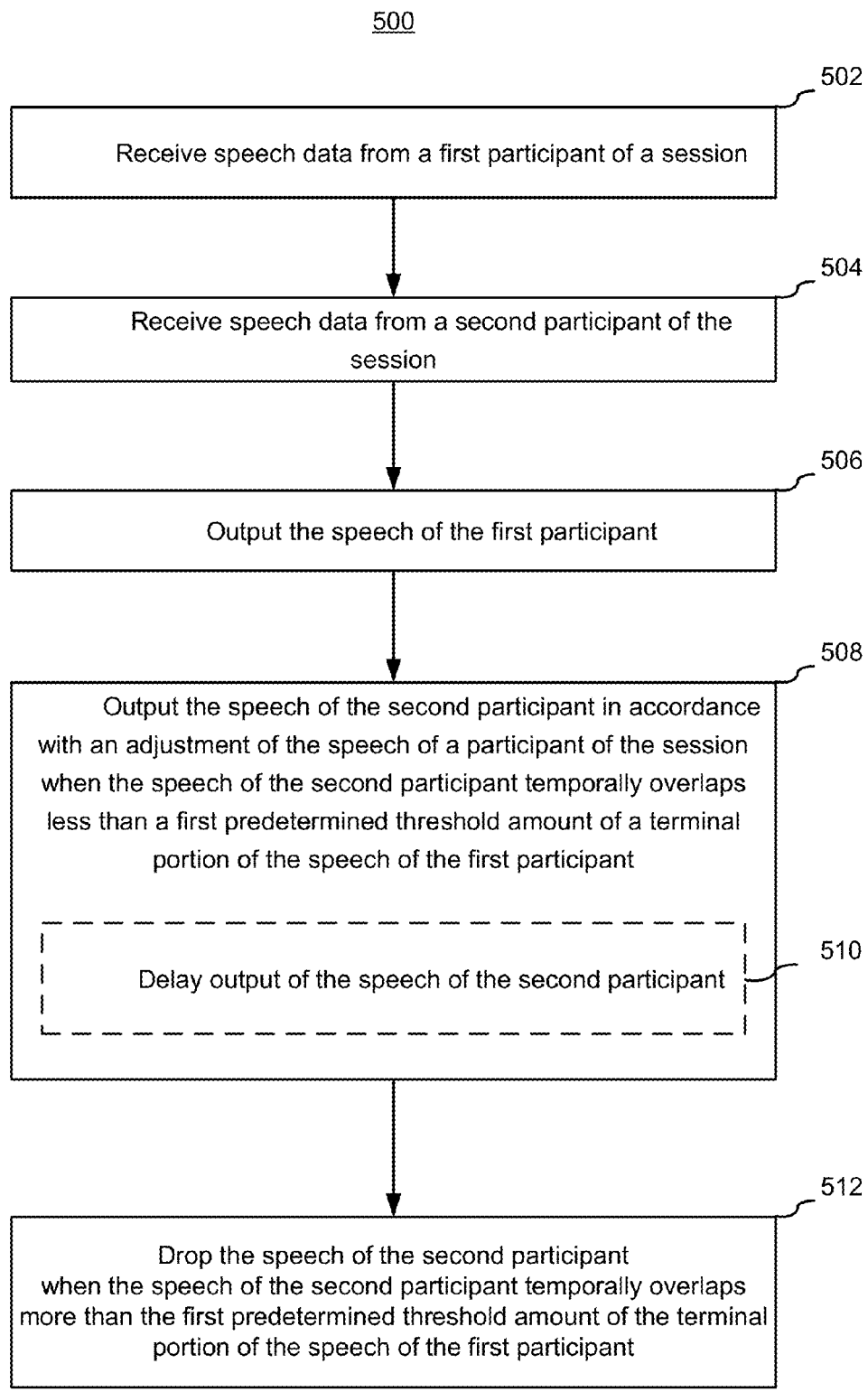
FIG. 5 is a flow diagram illustrating a method of handling concurrent speech, in accordance with some embodiments.

FIG. 5 includes a flowchart representing a method for handling concurrent speech at a server system, according to certain embodiments. Method 500 is, optionally, governed by instructions that are stored in a non-transitory computer readable storage medium and that are executed by one or more processors of one or more servers (e.g., Scheduling Server 106 in FIG. 3). In some implementations, each of the operations shown in FIG. 5 corresponds to instructions stored in a computer memory or non-transitory computer readable storage medium (e.g., Memory 306 of Scheduling Server 106 in FIG. 3). In some implementations, the non-transitory computer readable storage medium includes a magnetic or optical disk storage device, solid state storage devices such as Flash memory, or other non-volatile memory device or devices. In some implementations, the computer readable instructions stored on the non-transitory computer readable storage medium include one or more of: source code, assembly language code, object code, or other instruction format that is interpreted or executed by one or more processors. In various embodiments, some operations in method 500 may be combined and/or the order of some operations may be changed from the order shown in FIG. 5.

In some embodiments, a prior notion of conference dynamics (a Bayesian prior) is predicated in accordance with a Bayesian model (disclosed in more detail below), before a conference begins. In some embodiments, one or more scheduling options are determined, before a conference begins, based on the predicated conference dynamics. In some embodiments, a scheduling option that would maximize the performance of conferencing system is chosen before the conference begins.

In some embodiments, after a conference begins, Scheduling Server 106 first receives (502) speech data from a first participant of a session. In some embodiments, after receiving speech data from the first participant, Scheduling Server 106 also receives (504) speech data from a second participant of the session. In some situations, the speech of the first participant and the speech of the second participant temporally overlap each other, and, if outputted without adjustment, to either speech, would constitute concurrent speech. As discussed above, concurrent speech includes both speech made by different participants within a predefined threshold time interval, and speech received by Scheduling Server 106 within the predefined threshold time interval. In some embodiments, the predefined threshold time interval is calculated in accordance with a Bayesian model. In some embodiments, the Bayesian model includes information from Speech Recognition Module (126), Speech Transcription Module (128), and timing information of a speech. In some embodiments, the Bayesian model is used, by Scheduling Server 106, to determine what is likely to occur in a future conference or in a future speech by a particular participant, for example, how long a particular participant is likely to speak, and an estimated amount of overlap between speech by several particular participants. In some embodiments, the Bayesian model is updated periodically with new data from the above identified sources.

In some embodiments, the predefined threshold time interval is determined dynamically for individual speech. In some embodiments, the predefined threshold time interval includes a period of time in which Scheduling Server 106 decides to output a speech or to delay the speech until potential concurrent speech arrives. In some embodiments, the predefined threshold time interval during which a speech is delayed is determined in accordance with information from the Bayesian model, so that speech is only delayed, if at all, a minimum amount as possible, before Scheduling Server 106 decides whether to look for potential current speech.

In some embodiments, the predefined threshold time interval is a threshold period time having a duration selected from the range of 100 milliseconds to 1000 milliseconds. In some embodiments, the predefined threshold time interval is a threshold period time having a duration selected from the range of 1 second to 10 seconds. In some embodiments, the predefined threshold time interval is a threshold period time having a duration selected from the range of 5 seconds to 40 seconds. In some embodiments, the predefined threshold time interval is 10, 20, 30, 40, 50, 60, 70, or 80 milliseconds, or greater than 1 second.

In some embodiment, Scheduling Server 106 (506) outputs the speech of the first participant. In some embodiments, the speech of the first participant is outputted as soon as it is received, without delay. In some embodiments, the speech of the first participant is delayed, by Scheduling Server 106, for the predefined threshold time interval, to look for any potential concurrent speech. In some embodiments, within the predefined threshold time interval during when the speech of the first participant is being delayed, the speech of the second participant is also received. In some embodiments, the speech of the first and the second participants are thus considered concurrent because they are both received within the predefined threshold time interval.

In some embodiments, after the speech of the first participant is delayed for the predefined threshold time interval, during which no other speech is received (e.g., no concurrent speech occurs), the speech of the first participant is outputted with at an increased speed ("sped up"), to minimize any potential user perception about the delay. In some embodiments, one or more factors—e.g. factors from the Bayesian model—are used to dynamically determine (e.g., enlarge or reduce) the predefined threshold time interval, during which Scheduling Server 106 looks for possible concurrent speech.

In some situations, when the speech of the second participant temporally overlaps more than the first predetermined threshold amount of the terminal portion of the speech of the first participant, Scheduling Server 106 drops (512) the speech of the second participant. As discussed above, dropping a speech includes not outputting the speech, or a portion thereof, and outputting the speech to some but not all participants of a same session.

In some other situations, when the speech of the second participant temporally overlaps less than a first predetermined threshold amount of a terminal portion of the speech of the first participant, Scheduling Server 106 outputs (508) the speech of the second participant in accordance with an adjustment (e.g., by Output Adjustment Module 134) of the speech of a participant of the session.

In some embodiments, the adjustment of the speech of a participant of the session includes delaying (510) output of the speech of the second participant. In some embodiments, delaying output of the speech of second participant includes one or more of the following: (1) delaying output of the speech of the second participant until after the speech of the first participant has been outputted (e.g., speech of the second participant is outputted after the speech of the first participant); (2) delaying output of the speech of the second participant until an occurrence of a pause in the speech of the first participant (e.g., the speech of the second participant is delayed and outputted during a pause (sometimes called "free time") in the speech of the first participant); (3) delaying output of the speech of the second participant as a function of a relationship between the second participant and the first participant (e.g., delaying output of the second participant based on speaker roles associated with the first and second participants); (4) delaying output of the speech of the second participant as a function of a classification of the content of the speech of the second participant, as determined by Speech Recognition Module 126 and/or Speech Transcription Module 128 (e.g., whether the speech of the second participant is a question or a clarification to the speech of the first participant, or whether the speech of the second participant can be classified as interrupting speech or main speech, high priority speech or low priority speech, see more details below with references to FIGS. 7-10); (5) outputting the speech of the second participant in response to recognition of a prompt in the session (e.g., a predefined phrase, such as "any questions" or the like, a predefined sentence, such as "Next question please" or the like, a change of tone, or a change of an attendee's facial expression if the speech includes video information); and (6) outputting the speech of the second participant in response to a particular user input (e.g., a user click on an "immediate output" button displayed in Browser 106 or Conferencing Application 108, or a user pressing a similar button on a telephone or a mobile phone).

In other embodiments, the adjustment of the speech of a participant of the session also includes, using Output Adjustment Module 134 to accelerate ("speed up") or slow ("slow down") the output of the speech of the first participant. In some embodiments, where some speakers are slow speakers, and some other speakers are fast speakers, speech by the slow speakers is accelerated more than that of the fast speakers. In some embodiments, whether a speaker is a fast speaker or a slow speaker is determined in accordance with a transcript of the speaker's speech. In some embodiments, whether a speaker is a fast speaker or a slow speaker is determined with a profile recorded for the speaker base upon the speaker's past speech. In some embodiments, speech that has been delayed in some manner (e.g., due to fact that speech has a lower priority) is outputted at an increase speed ("sped up") to minimize user perception about the delay.

In some embodiments, "speeding up" or "slowing down" the output of the speech of the first participant is achieved by accelerating or slowing down the speech of the first participant using an audio timescale-pitch modification algorithm, or (ii) by shortening or removing one or more pauses within the speech. In some other embodiments, the adjustment of the speech of a participant of the session further includes (i) cutting off the speech of the first participant when a length of the speech of the first participant exceeds a predetermined time threshold, and (ii) outputting the speech of the second participant when the speech of the first participant has been cut off. In other words, a long speech may be cut off, at least temporarily, in order to output another speech that has been delayed for too long. In some embodiments, the predetermined time threshold is an amount of time in the range of 100 milliseconds to 1000 milliseconds. In some embodiments, the predetermined time threshold is a period time having a duration selected from the range of 1 second to 10 seconds. In some embodiments, the predetermined time threshold is in the range of 5 seconds to 40 seconds. In some embodiments, the predetermined time threshold is 10, 20, 30, 40, 50, 60, 70, or 80 milliseconds, or greater than 1 second.

It should be understood that the particular order in which the operations in FIG. 5 have been described are merely exemplary and are not intended to indicate that the described order is the only order in which the operations could be performed. One of ordinary skill in the art would recognize various ways to reorder the operations described herein. Additionally, it should be noted that details of other processes described herein with respect to methods 500 (described herein with reference to FIG. 5) are also applicable in an analogous manner to method 400 described above with respect to FIG. 4. For example, the speech data and its receipt thereof, speech and its output thereof, adjusting or dropping of a speech, and speech overlapping described above with reference to method 500 may have one or more of the characteristics of the speech data and its receipt thereof, speech and its output thereof, adjusting or dropping of a speech, and speech overlapping described herein with reference to method 400. For brevity, these details are not repeated here.

Figure 6:
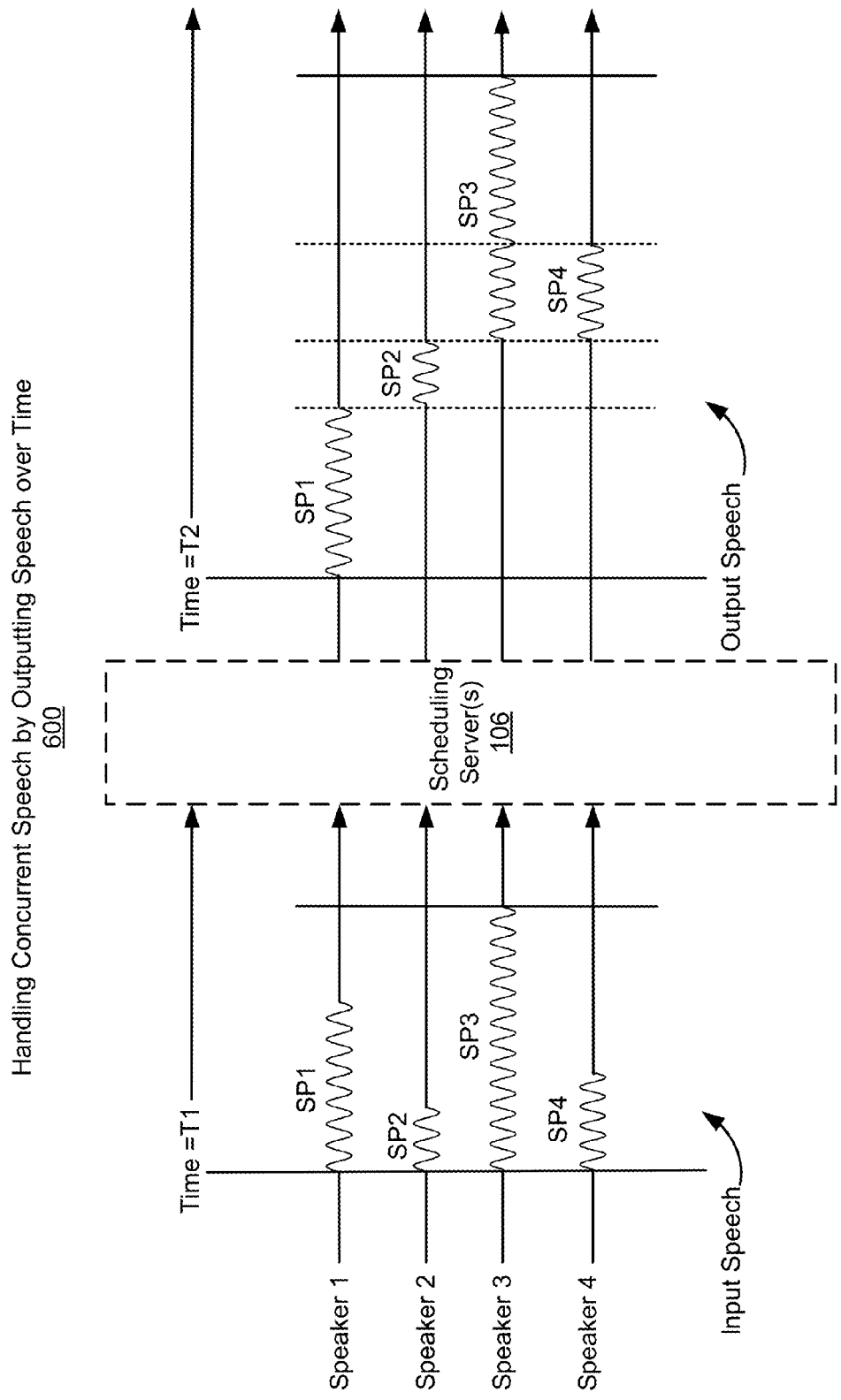
FIG. 6 is a block diagram illustrating an example of handling concurrent speech, in accordance with some embodiments.

FIG. 6 illustrates an example of handling concurrent speech, in accordance with some embodiments. As shown in FIG. 6, four speakers (Speakers 1-4) speak, through one or more Clients 102, at or around the same time (Time=T1). Speech data (SP 1-4)—including audio and/or video information, and corresponding meta-data—from Speakers 1-4 is then transmitted to Scheduling Server 106. Scheduling Server 106 processes the speech data, and outputs speech with or without adjustments.

As show in FIG. 6, SP 1 (the speech of Speaker 1) is outputted at or around Time=T2. In some embodiments, T2 equals to T1. In other words, SP 1 is outputted as it is received (e.g., without delay). In other embodiments, T2 is after T1. In some situations, the time interval between T1 and T2 results from non-artificial delays (or inherent delays), such as network latency (such as latency within Communication Network 104 (FIG. 1)), and/or device latency (such as processing latency within Scheduling Server 106 or Client(s) 102). In other situations, the time interval between T1 and T2 results from artificial delays, such as delays internationally or deliberately added by Scheduling Server 106.

After the output of SP 1, SP 2 (the speech of Speaker 2) is also outputted. In this example, SP 2 is outputted immediately after SP 1, for example, to minimize system idleness, or to achieve a particular communication purpose, such as maintaining coherency between speech. In other embodiments, an artificial delay is added between the end of SP 1 and the beginning of SP 2, to, for example, provide clarity.

As shown in FIG. 6, after SP 2 is outputted, SP 3 and SP 4 are outputted at or around the same time, as concurrent or overlapping speech. In some embodiments, a predefined degree of concurrency or overlapping is allowed, for example, when the volumes of speech is high, in order to increase throughput. In some embodiments, the predefined degree of concurrency is modifiable, either by users of Client(s) 102, through an interface control (e.g., a button) displayed in Browser 106 or Conferencing Application 108, or by Scheduling Server 106, in accordance with Scheduling Parameters 130 and/or speech meta-data. Referring to FIG. 6, in some alternative embodiments, SP 3 or SP 4 is dropped.

Figure 7:
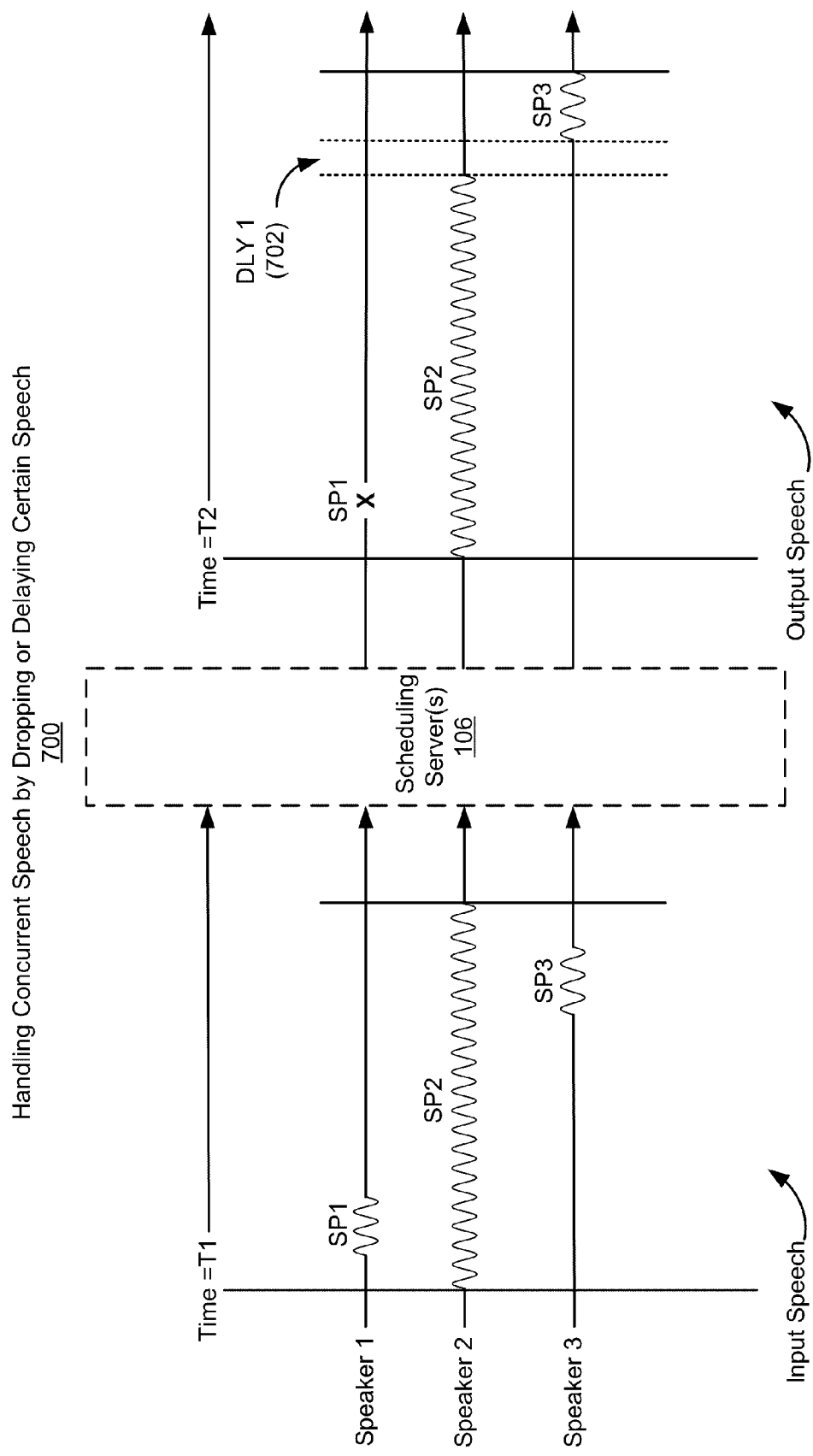
FIG. 7 is a block diagram illustrating a second example of handling concurrent speech, in accordance with some embodiments.

FIG. 7 illustrates a second example of handling concurrent speech, in accordance with some embodiments. In this example, to handle concurrent speech, certain speech is delayed or dropped in accordance speech meta-data.

As shown in FIG. 7, three speakers (Speakers 1-3) speak at or around the same time (Time=T1). Speech data (SP 1-3)—including audio and/or video information, and corresponding meta-data—from Speakers 1-3 is transmitted to Scheduling Server(s) 106. Scheduling Server 106 processes the speech data, and outputs corresponding speech with various adjustments.

Based on the received speech data, Scheduling Server 106 classifies SP 2 (the speech from Speaker 2) as main speech. In accordance with this classification, SP 2 is outputted first and without adjustment (e.g., as is). The classification of a speech, in some embodiments, is based on, at least in part, speech data. For example, speech is classified as main speech if the content of the speech includes terms that meet a predefined set of importance criteria. In another example, speech is classified as main speech if the speech meta-data includes information (e.g., length of the speech, or timing of the speech) that meets a predefined set of importance criteria. In other embodiments, the speech classification is made independent of speech data, such as based on preexisting relationships between the speakers. For example, SP 2 is classified as a main speech because Speaker 2 is a superior of Speakers 1 and 3 within an organization.

Before or during the output of SP 2, Scheduling Server 106 classifies SP 1 as an interrupting speech, because SP 2 overlaps an early portion of SP 1, a main speech. In some embodiments, an interrupting speech is dropped or delayed until a pause within the main speech is detected. Here, because SP 1 includes no pause, and because SP 2 overlaps an early portion of SP 1 (interrupting SP 1 "too early"), SP 2 is dropped (shown as "X").

In some embodiments, speech is dropped by the Scheduling Server 106 under a predetermined set of speech management policies. In some embodiments, the set of speech management policies includes a determination that the speech is interrupting speech and overlaps an early portion of the main speech (e.g., interrupting too early). In other embodiments, the speech management policies include a determination that speech has been delayed for more than a predetermined amount of time. In implementations, where speech is placed in a queue for scheduled output, the speech management policies include a determination that speech has been placed in the output queue for more than a predetermined amount of time. In other words, speech is dropped when it is deemed "old." Old speech is dropped, in some situations, because it may have become irrelevant to the session, due to a shift in conversation focus. In some embodiments, speech is deemed old when it is delayed by more than 1 second, more than 5 seconds, more than 10 seconds, more than 20 seconds, or more than one minute.

In some embodiments, speech is also dropped in response to a particular user input, such as a user click on a "drop" button in Browser 106 or Conferencing Application 108. In some situations, dropping speech increases communication effectiveness and speech clarity, by preventing important speech from being interrupted at an early stage and thus having to be repeated before it is fully delivered.

Before or during the output of SP 2, Scheduling Server 106 also determines that SP 3 overlaps a late portion of SP 2. In accordance with this determination, SP 3 is outputted after SP 2 with adjustments. In this example, Scheduling Server 106 intentionally or deliberately delays the output of SP 3 (the speech of Speaker 3) for a time interval, DLY 1 (702). In some embodiments, the amount of delay intentionally added is proportional to the content or classification of a speech. For example, a greater delay between important speech and interrupting speech is desirable, in order to give the audience sufficient time to digest the content of the important speech. In another example, however, a smaller delay or no delay between a statement and a clarification thereto is desirable, in order to minimize confusion.

Figure 8:
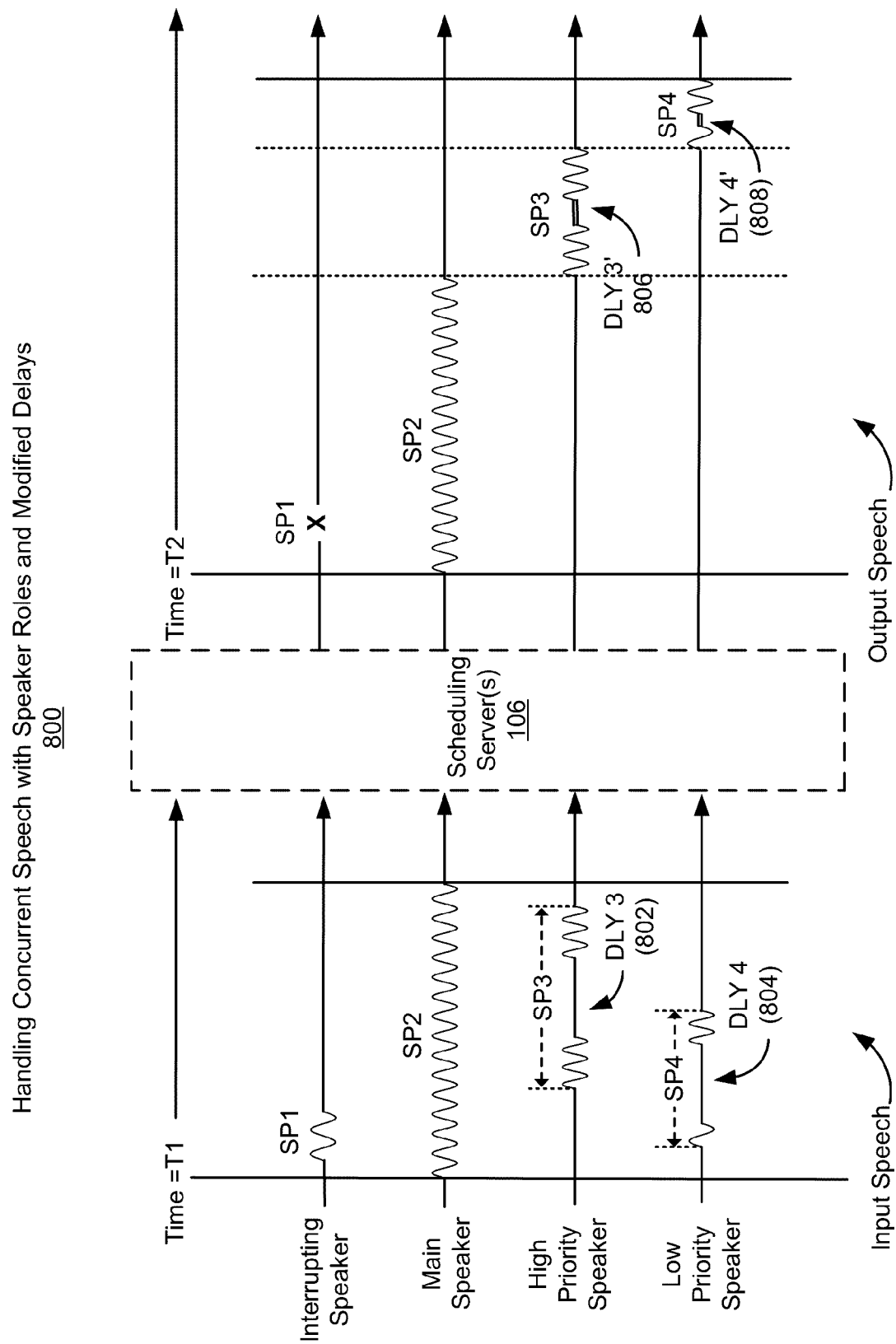
FIG. 8 is a block diagram illustrating a third example of handling concurrent speech, in accordance with some embodiments.

FIG. 8 illustrates a third example of handling concurrent speech, in accordance with some embodiments. In this example, concurrent speech is handled in accordance with speaker roles, and with modified delays.

As shown in FIG. 8, four speakers with different roles—Main Speaker, Interrupting Speaker, High Priority Speaker and Low Priority Speaker—speak at or around the same time (Time=T1). In some embodiments, speaker roles are determined independent of speech data, for example, based on pre-existing relationship between speakers. In other embodiments, speaker roles are determined based at least in part on speech data, such as the content of a speech, a timestamp associated with a speech, the length of a speech, and a classification of a speech. In some embodiments, speech priorities are derived from speaker roles or speaker priorities.

In the example shown in FIG. 8, SP 2 (the speech of Main Speaker) is received and outputted without adjustment. SP 1 (the speech of Interrupting Speaker) is dropped ("X") because it "interferes" with Main Speaker by overlapping an early portion of SP 2.

In some embodiments, speech having a priority equal to or higher than a predefined threshold priority is not dropped, even though the speech overlaps the main speech. For example, SP 3 (the speech of the High Priority Speaker) is not dropped, although SP 3 (like SP 1) also overlaps a portion of SP 2. Because SP 3 is from a speaker of high priority, instead of dropping SP 3, Scheduling Server 106 outputs SP 3 after SP 2. Similarly, SP 4 (the speech of Low Priority Speaker), is also not dropped. In some embodiments, higher priority speech is outputted before lower priority speech. For example, SP 4 is outputted after SP 3, because SP 3 is of a higher priority than SP 4.

In some embodiments, in accordance with a determination that the main speech exceeds a predetermined length, speech outputted after the main speech is adjusted by shortening delays included therein (e.g., removing pauses within the main speech). In one such example, SP 3 and SP 4, both include pauses: DLY 3 (802) and DLY 4 (804), respectively. Because SP 3 and SP 4 are both outputted after SP 2 (the main speech), and SP 2 exceeds a predetermined threshold length, pauses within SP 3 and SP 4—DLY 3 (802) and DLY 4 (804)—are shortened—into DLY 3' (806) and DLY 4' (808), respectively. This approach not only increases speech clarity by dropping interrupting speech, but also enhances user experience by outputting a high priority speech before a low priority speech. In some embodiments, the predetermined threshold length is an amount of time in the range of 100 milliseconds to 1000 milliseconds. In some embodiments, the predetermined threshold length is a period time having a duration selected from the range of 1 second to 10 seconds. In some embodiments, the predetermined threshold length is in the range of 5 seconds to 40 seconds. In some embodiments, the predetermined threshold length is 10, 20, 30, 40, 50, 60, 70, or 80 milliseconds, or greater than 1 second.

In some embodiments, the user interface ("UI") of Browser 150 or Conferencing Application 108, at Client 102, is determined in accordance with speaker roles. For example, in some implementations, the user interface of a main speaker includes a "drop" button that, when clicked, drops an ongoing speech by another speaker (so as to enable the main speaker to interrupt other speakers whenever the main speaker sees fit). In some implementations, in accordance with a determination that a speaker is classified as an interrupting speaker or low priority speaker, the "drop" button in that speaker's Browser 150 or Conferencing Application 108 is made unavailable (e.g., "greyed out"), so as avoid a situation where an interrupting speaker or low priority speaker can interfere with a main speaker or a high priority speaker.

In some embodiments, the user interface of Browser 150 or Conferencing Application 108 also includes one or more user controls that provide usage information of a conferencing system, and/or status information of participant(s) or speech, in a session. The usage information, in some implementations, includes: the number of speech currently awaiting output (e.g., the size of an output queue). In some embodiments, a conversion of usage information is included. For example, the size of an output queue is converted and displayed in terms of the total length of speech currently awaiting output (e.g., 10 seconds when an output queue is nearly full or 10 milliseconds when the queue is nearly empty).

The status information of participant(s) or speech in a session, in some implementations, includes: the position of a delayed speech in an output queue (e.g., the number of speech in the same output queue ahead of the delayed speech), the number of speech being delayed for a particular speaker (e.g., the number or length of speech being delayed for a low priority speaker), information indicating whether future speech would "overwrite" a delayed speech by a particular participant (e.g., a flashing red light above an icon representing a low priority speaker indicating that if an attendee speaks now, the particular participant's speech would cause delayed speech by the low priority speaker to be further delayed or even dropped), information indicating whether delayed speech is being dropped (e.g., a fast flashing red light indicating delayed speech is being dropped), information indicating whether the number of participant's speech currently being delayed is close to or has exceeded a threshold number (e.g., a counter or progress bar indicating how "crowded" an output queue is), information indicating a likelihood that future speech is going to be delayed (e.g., a slow flashing yellow light indicating if a participant speaks now, the participant's speech will likely be delayed), and information indicating whether a real-time transcription is available to a participant of a conferencing system (e.g., whether a "transcribe in a chat window" button is clickable or "greyed out").

The display of user controls that provide usage or status information (or feedback) reduces user frustration, as users are made aware of the status of their speech, and/or status of speech by other participants in the same session, thereby enhancing user experience of a conferencing system.

Figure 9:
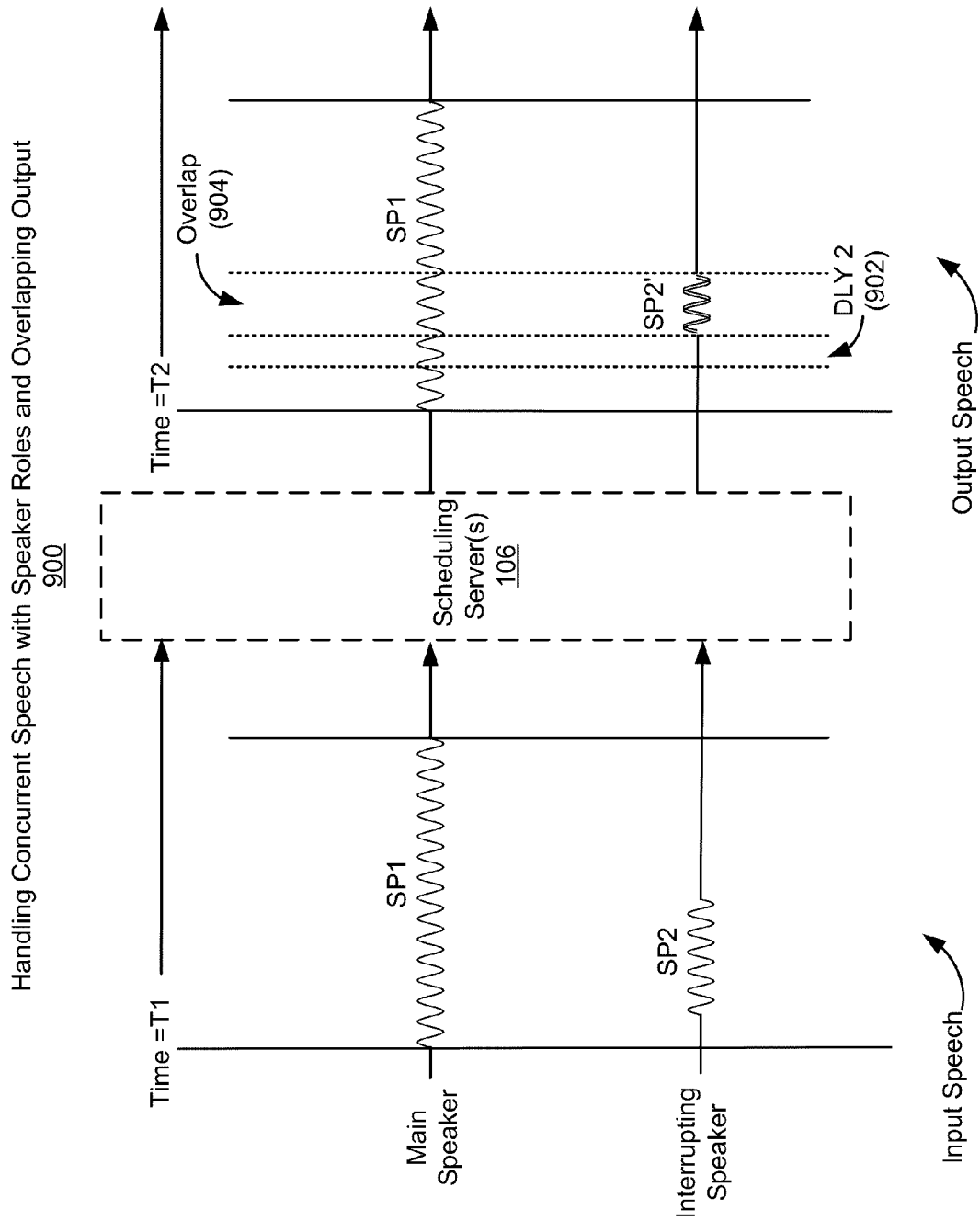
FIG. 9 is a block diagram illustrating a fourth example of handling concurrent speech, in accordance with some embodiments.

FIG. 9 illustrates a fourth example of handling concurrent speech, in accordance with some embodiments. In this example, concurrent speech is handled in accordance with speaker roles, and with overlapping output.

In the example shown in FIG. 9, two speakers, Main Speaker and Interrupting Speaker, speak at or around the same time. Speech data is transmitted to Scheduling Server 106 for processing and scheduled output. As discussed above, speaker roles and speech priorities can be determined based at least in part on speech data, or independent of speech data.

In this example, because SP 1 is speech from Main Speaker, SP 1 is output first, and without modification or adjustment. In accordance with a determination that the length of SP 1 exceeds a predetermined threshold length and there is no pause within SP 1, SP 2 (the speech from Interrupting Speaker) is outputted concurrently with a portion of SP 1. In other words, in situations where a main speaker has been speaking for too long, without pause, or an indication to stop, speech by another speak can be outputted, although it would overlap a portion of the main speech. This approach ensures that speech from a speaker, regardless of its priority, is always heard within a time period acceptable to users.

SP 2 is outputted, however, with delay and adjustment, as SP 2'. As shown in FIG. 9, SP 2 is outputted with delay, DLY 2 (902). In some embodiments, a delay includes a period of time over which Scheduling Server 106 attempts to detect a pause within an ongoing speech. In other embodiments, the delay includes a period of time which Scheduling Server 106 has reserved for uninterrupted main speech, so that at least an early portion, and sometimes, also an important portion, of the main speech is delivered without overlap or interruption.

In some embodiments in accordance with the example presented in FIG. 9, SP 2 is also outputted with adjustments to its speed. In FIG. 9, Scheduling Server 106, using Output Adjustment Module 134, increases the speed of SP 2. SP 2 is outputted in a period of time less than its normal length (sometimes also called "contracted"), using a pitch conservation algorithm.

As also shown in FIG. 9, during Overlap (904), speech SP 1 and SP 2' are outputted concurrently. After SP 2' is outputted, SP 1 continues to be outputted without adjustment.

In some embodiments, a delay added to an interrupting speech, for example DLY 2 (902), is determined based at least in part on speech data associated with a speech, or alternatively, independent of speech data. For example, if a speech recognition analysis of SP 2 indicates that SP 2 represents a question that specifically relates to a later portion of SP 1 that has not yet been outputted, SP 2 is delayed, e.g., not outputted, until after the later portion of SP is outputted, to promote efficiency and clarity. In other implementations, a delay added to an interrupting speech is determined in accordance with a pre-existing relationship between speakers. For example, SP 2 is delayed less, when Interrupting Speaker is a superior (e.g., a manger) of Main Speaker (e.g., a rank and file employee), than when Interrupting Speaker is a peer to Main Speaker.

In some embodiments, Overlap (904) is determined based at least in part on speech data, or alternatively, independent of speech data. In some implementations, Overlap (904) corresponds to a portion of the main speech that fails a predefined set of importance criteria. In other words, SP 2' is allowed to overlap with a relatively less important portion of main speech SP 1. In some implementations, Overlap (904) is proportional or inversely proportional to the length of the speech. For example, the length of Overlap (904) is a predetermined percentage of the length of a main speech, or the predetermined percentage of the length of an interrupting speech, or both.

Figure 10:
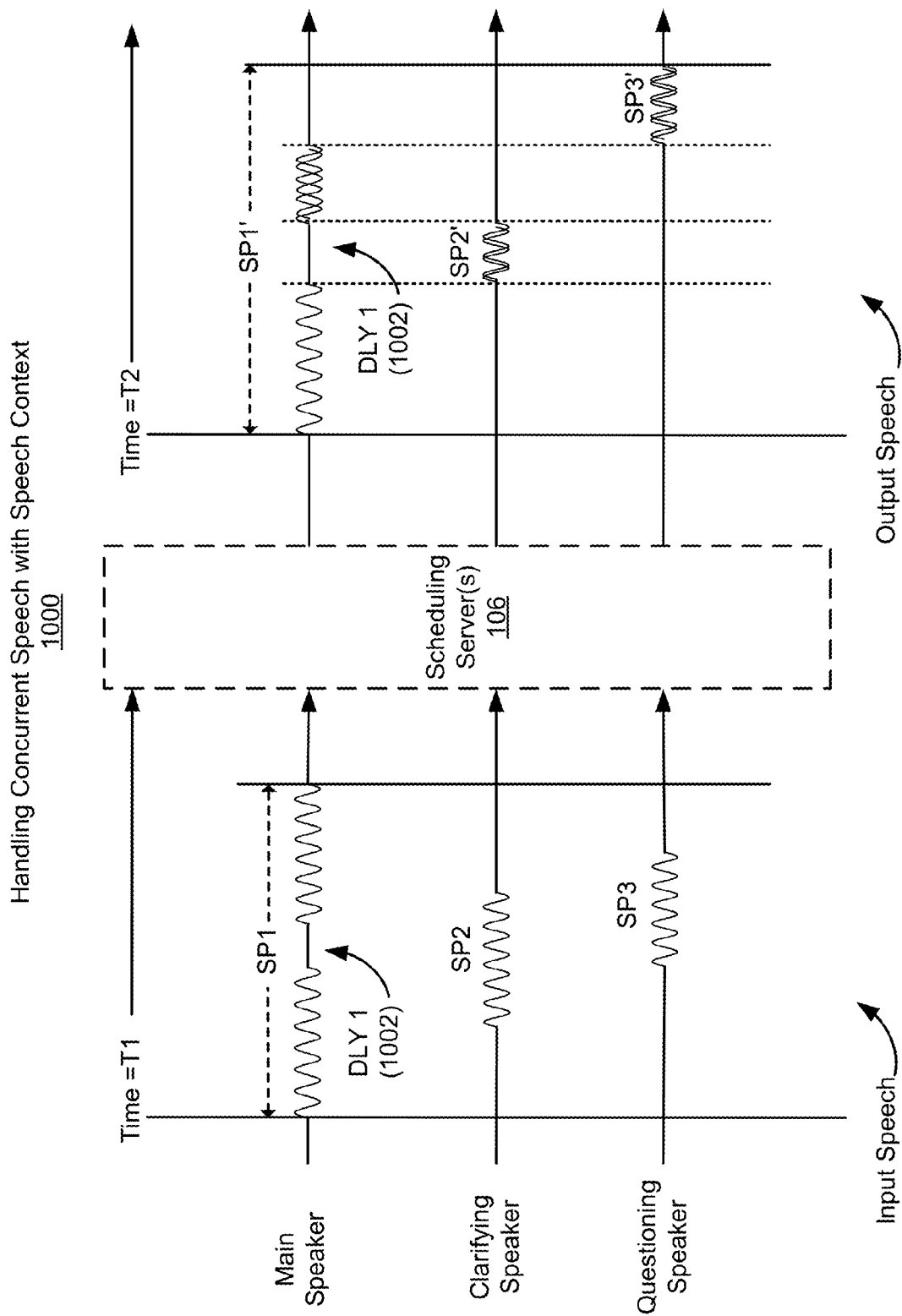
FIG. 10 is a block diagram illustrating a fifth example of handling concurrent speech, in accordance with some embodiments.

FIG. 10 illustrates a fifth example of handling concurrent speech, in accordance with some embodiments. In this example, concurrent speech is handled in accordance with speech context and/or classification.

In the example shown in FIG. 10, three speakers speak at or around the same time. Speech data is transmitted to Scheduling Server 106 for processing and scheduled output. After applying speech recognition and/or speech transcription techniques (for example at Speech Recognition Module 126 and Speech Transcription Module 128, respectively), speech SP 1-3 is classified into three categories: Main Speech, Clarifying Speech, and Questioning Speech. In some embodiments, a speaker role is assigned in accordance with a speech classification.

In some embodiments, speech in different categories is assigned different priorities, and their output is adjusted based at least in part on their respective priorities. Speech in Main Speech category, in some situations, is assigned a higher priority than speech in other categories, because main speech is considered more important than a question or a clarification. In other situations, speech in the Clarifying Speech category is assigned a higher priority than speech in Questioning Speech category, because a clarification, sometimes, directly addresses a question, and thus should be outputted before the question to reduce redundancy.

In the example shown in FIG. 10, main speech SP 1 includes two portions separated by a pause, DLY 1 (1002). The first portion of main speech is outputted, without delay or adjustment. After detecting that clarifying speech SP 2 relates to the first portion of SP 1 (for example, by clarifying a term used therein), clarifying speech SP 2 is outputted with adjustments, as SP 2', during a pause in SP 1, e.g., DLY 1 (1002). Because the length of SP 2 exceeds the length of the pause, the speed of SP 2 is increased, using a pitch conserving algorithm, so that SP 2's is fully outputted within the pause DLY 1 (1002).

After adjusted clarifying speech SP 2' is outputted, the second portion of the main speech SP 1 is outputted, also with adjustment. The second portion of SP 1 is also "sped up." After the second portion of SP 1 is outputted, questioning speech SP 3 is also outputted as at increased speed, as SP 3'.

In some embodiments, speech, or a portion thereof, is adjusted in accordance with the content of other speech, which provides a context for the speech. For example, the second portion of main speech SP 1, including a clarification similar to SP 2', is sped up, because the second portion of main speech SP 1, in light of the prior output of clarifying speech SP 2', has become less important, and needs not be repeated or detailed.

In some embodiments, questioning speech is also adjusted in accordance with the content of another speech (e.g., speech context). For example, when a question included in a portion of a questioning speech has already been answered or addressed by a prior speech, the corresponding portion of the questioning speech is sped up to reduce redundancy and increase throughput.

In some embodiments, the output of questioning speech is delayed more than clarifying speech and main speech. In other words, in some embodiments, questioning speech is not outputted until main speech and/or clarifying speech is outputted. This approach can increase overall effectiveness, because a question included in questioning speech, in some situations, is answered in a clarifying speech or a later portion of the main speech. In other embodiments, questing speech is outputted before clarifying speech or a portion of the main speech, when the questioning speech includes an important question that needs to be addressed or made known as early as possible.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method comprising:
    at a system comprising one or more processors and a memory storing one or more programs for execution by the one or more processors:
    receiving speech data from a first participant of a session;
    receiving speech data from a second participant of the session; and
    determining whether the speech data from the second participant temporally overlaps the speech data from the first participant, wherein
        when the speech data from the second participant does not temporally overlap the speech data from the first participant, the speech data of the first participant is outputted and then the speech data of the second participant is outputted,
        when the speech data from the second participant temporally overlaps the speech data from the first participant, a length of time of the speech data of the first participant is determined, wherein
            when the length of time is less than a first predetermined threshold amount, the speech data of the first participant is outputted and then the speech data of the second participant is outputted in accordance with an adjustment of the speech of one or more participants of the session that includes delaying output of the speech data of the second participant until after the speech data of the first participant has been outputted; and when the length of time is more than the first predetermined threshold amount, the speech data of the first participant and the speech data of the second participant is concurrently outputted.

2. The method of claim 1, wherein, when the speech data of the first participant and the speech data of the second participant are outputted concurrently, the speech data of the second participant is delayed by an amount that is determined by a relationship between the first participant and the second participant.

3. The method of claim 1, wherein, when the speech data of the first participant and the speech data of the second participant are outputted concurrently, the speech data of the second participant is delayed by an amount that is determined by speech recognition analysis of the speech data of the first participant or the second participant.

4. The method of claim 1, wherein, when the speech data of the first participant and the speech data of the second participant are outputted concurrently, the speech data of the second participant is delayed by an amount.

5. The method of claim 1, wherein delaying output of the speech data of the second participant comprises delaying output of the speech data of the second participant as a function of a classification of the content of the speech data of the second participant.

6. The method of claim 5, wherein the classification of the content of the speech data of the second participant is done by speech recognition and transcription of the content of the speech data of the second participant.

7. The method of claim 1, wherein delaying output of the speech data of the second participant comprises outputting the speech data of the second participant in response to recognition of a prompt in the session.

8. The method of claim 1, wherein delaying output of the speech data of the second participant comprises outputting the speech data of the second participant in response to a user input.

9. The method of claim 1, wherein outputting the speech data of the second participant in accordance with an adjustment of the speech of one or more participants of the session further comprises speeding up the speech of the first participant.

10. The method of claim 9, wherein speeding up the speech of the first participant includes accelerating the speech of the first participant using an audio timescale-pitch modification algorithm.

11. The method of claim 9, wherein speeding up the speech of the first participant includes shortening or removing one or more pauses within the speech of the first participant.

12. The method of claim 1, the method further comprising:

receiving speech data from a third participant of the session, wherein the speech of the third participant temporally overlaps, at least partially, with the speech of the first participant and the speech of the second participant; and the adjustment of the speech of one or more participants of the session comprises outputting the speech data of the second participant before the speech data of the third participant when a priority of the second participant in the session is higher than a priority of the third participant.

13. The method of claim 12 wherein the priority of the second participant and the priority of the third participant is determined on a FIFO basis, a role-based basis, a social network status basis, or a number of votes.

14. A server system, comprising:
one or more processors;
memory; and
one or more programs, wherein the one or more programs are stored in the memory and configured to be executed by the one or more processors, the one or more programs including instructions for:
receiving speech data from a first participant of a session;
receiving speech data from a second participant of the session; and
determining whether the speech data from the second participant temporally overlaps the speech data from the first participant, wherein
when the speech data from the second participant does not temporally overlap the speech data from the first participant, the speech data of the first participant is outputted and then the speech data of the second participant is outputted,
when the speech data from the second participant temporally overlaps the speech data from the first participant, a length of time of the speech data of the first participant is determined, wherein
when the length of time is less than a first predetermined threshold amount, the speech data of the first participant is outputted and then the speech data of the second participant is outputted in accordance with an adjustment of the speech of one or more participants of the session that includes delaying output of the speech data of the second participant until after the speech data of the first participant has been outputted; and
when the length of time is more than the first predetermined threshold amount, the speech data of the first participant and the speech data of the second participant is concurrently outputted.

15. The server system of claim 14, wherein, when the speech data of the first participant and the speech data of the second participant are outputted concurrently, the speech data of the second participant is delayed by an amount that is determined by a relationship between the first participant and the second participant.

16. The server system of claim 14, wherein, when the speech data of the first participant and the speech data of the second participant are outputted concurrently, the speech data of the second participant is delayed by an amount that is determined by speech recognition analysis of the speech data of the first participant or the second participant.

17. The server system of claim 14, wherein, when the speech data of the first participant and the speech data of the second participant are outputted concurrently, the speech data of the second participant is delayed by an amount.

18. A non-transitory computer readable storage medium storing one or more programs, the one or more programs comprising instructions, which when executed by a computer system with one or more processors, cause the computer system to:
receive speech data from a first participant of a session;
receive speech data from a second participant of the session; and
determine whether the speech data from the second participant temporally overlaps the speech data from the first participant, wherein when the speech data from the second participant does not temporally overlap the speech data from the first participant, output the speech data of the first participant and then output the speech data of the second participant, when the speech data from the second participant temporally overlaps the speech data from the first participant, a length of time of the speech data of the first participant is determined, wherein when the length of time is less than a first predetermined threshold amount, output the speech data of the first participant and then output the speech data of the second participant in accordance with an adjustment of the speech of one or more participants of the session that includes delaying output of the speech data of the second participant until after the speech data of the first participant has been outputted; and when the length of time is more than the first predetermined threshold amount, output the speech data of the first participant and output the speech data of the second participant concurrently.

19. The computer readable medium of claim 18, wherein, when the speech data of the first participant and the speech data of the second participant are outputted concurrently, the speech data of the second participant is delayed by an amount that is determined by a relationship between the first participant and the second participant.

20. The computer readable medium of claim 18, wherein, when the speech data of the first participant and the speech data of the second participant are outputted concurrently, the speech data of the second participant is delayed by an amount that is determined by speech recognition analysis of the speech data of the first participant or the second participant.

* * * * *